United States Patent
von Oepen et al.

(10) Patent No.: US 11,484,408 B2
(45) Date of Patent: Nov. 1, 2022

(54) DELIVERY CATHETER DISTAL CAP

(71) Applicant: Cephea Valve Technologies, Inc., Santa Clara, CA (US)

(72) Inventors: Randolf von Oepen, Aptos, CA (US); Sean A. McNiven, Menlo Park, CA (US); Ken C. Salvador, Hayward, CA (US)

(73) Assignee: Cephea Valve Technologies, Inc., Santa Clara, CA (US)

( * ) Notice: Subject to any disclaimer, the term of this patent is extended or adjusted under 35 U.S.C. 154(b) by 431 days.

(21) Appl. No.: 16/828,112

(22) Filed: Mar. 24, 2020

(65) Prior Publication Data

US 2020/0222183 A1  Jul. 16, 2020

Related U.S. Application Data

(63) Continuation of application No. 15/662,014, filed on Jul. 27, 2017, now Pat. No. 10,631,981.

(Continued)

(51) Int. Cl.
*A61F 2/24* (2006.01)
*A61F 2/95* (2013.01)
(Continued)

(52) U.S. Cl.
CPC .......... *A61F 2/2427* (2013.01); *A61F 2/2436* (2013.01); *A61F 2/2466* (2013.01); *A61F 2/95* (2013.01); *A61M 25/0147* (2013.01); *A61F 2002/9505* (2013.01); *A61F 2002/9511* (2013.01); *A61M 39/10* (2013.01)

(58) Field of Classification Search
CPC ........ A61F 2/95; A61F 2/2466; A61F 2/2427; A61F 2/2436; A61F 2002/9505; A61F 2002/9511; A61M 25/0147; A61M 39/10
See application file for complete search history.

(56) References Cited

U.S. PATENT DOCUMENTS

| 4,728,319 A | 3/1988 | Masch |
| 5,059,213 A | 10/1991 | Chesterfield et al. |

(Continued)

FOREIGN PATENT DOCUMENTS

| EP | 1980288 | 10/2008 |
| EP | 2537487 | 12/2012 |

(Continued)

OTHER PUBLICATIONS

Takizawa H et al: "Development of a microfine active bending catheter equipped with MIF tactile sensors",Micro Electro Mechanical Systems, 1999. MEMS '99. Twelfth IEEE International Conference on Orlando, FL, USA Jan. 17-21, 1999, Piscataway, NJ, USA,IEEE, US,Jan. 17, 1999 (Jan. 17, 1999), pp. 412-417, XP010321677, ISBN: 978-0-7803-5194-3 figures 1-3.

(Continued)

*Primary Examiner* — Julian W Woo
(74) *Attorney, Agent, or Firm* — Workman Nydegger

(57) ABSTRACT

An intravascular device delivery system includes a distal end cap to connect an elongated member of the intravascular device delivery system to an intravascular device. The distal end cap includes at least one connection member radially movable relative to the distal end cap that is configured to engage with a complimentary recess in the intravascular device.

20 Claims, 3 Drawing Sheets

Related U.S. Application Data

(60) Provisional application No. 62/422,426, filed on Nov. 15, 2016.

(51) Int. Cl.
*A61M 25/01* (2006.01)
*A61M 39/10* (2006.01)

(56) References Cited

U.S. PATENT DOCUMENTS

| | | |
|---|---|---|
| 5,236,450 A | 8/1993 | Scott |
| 5,325,845 A | 7/1994 | Adair |
| 5,669,919 A | 9/1997 | Sanders et al. |
| 5,807,405 A | 9/1998 | Vanney et al. |
| 5,855,601 A | 1/1999 | Bessler et al. |
| 5,902,334 A | 5/1999 | Dwyer et al. |
| 5,906,642 A | 5/1999 | Caudillo et al. |
| 6,458,137 B1 | 10/2002 | Klint |
| 7,172,617 B2 | 2/2007 | Colgan et al. |
| 7,232,462 B2 * | 6/2007 | Schaeffer ............ A61F 2/0105 606/200 |
| 7,344,553 B2 | 3/2008 | Opolski et al. |
| 7,736,388 B2 | 6/2010 | Goldfarb et al. |
| 7,837,727 B2 | 11/2010 | Goetz et al. |
| 7,988,724 B2 | 8/2011 | Salahieh et al. |
| 7,993,303 B2 | 8/2011 | Von Oepen et al. |
| 8,157,852 B2 | 4/2012 | Bloom et al. |
| 8,911,455 B2 | 12/2014 | Quadri et al. |
| 8,926,692 B2 | 1/2015 | Dwork |
| 9,339,378 B2 | 5/2016 | Quadri et al. |
| 9,370,423 B2 | 6/2016 | Ryan |
| 9,393,112 B2 | 7/2016 | Tuval et al. |
| 9,399,112 B2 | 7/2016 | Shevgoor et al. |
| 9,668,859 B2 | 6/2017 | Kheradvar et al. |
| 9,687,373 B2 | 6/2017 | Vad |
| 9,693,862 B2 | 7/2017 | Campbell et al. |
| 9,801,745 B2 | 10/2017 | Wubbeling et al. |
| 10,631,981 B2 | 4/2020 | von Oepen et al. |
| 2004/0049207 A1 | 3/2004 | Goldfarb et al. |
| 2005/0038383 A1 | 2/2005 | Kelley et al. |
| 2005/0085903 A1 | 4/2005 | Lau |
| 2005/0137695 A1 | 6/2005 | Salahieh et al. |
| 2005/0283231 A1 | 11/2005 | Haug et al. |
| 2007/0173757 A1 | 7/2007 | Levine et al. |
| 2007/0203561 A1 | 8/2007 | Forster et al. |
| 2007/0260225 A1 | 11/2007 | Sakakine et al. |
| 2009/0099554 A1 | 4/2009 | Forster et al. |
| 2009/0240326 A1 | 9/2009 | Wilson et al. |
| 2010/0004739 A1 | 1/2010 | Vesely |
| 2010/0217261 A1 | 8/2010 | Watson |
| 2010/0249894 A1 | 9/2010 | Oba et al. |
| 2010/0331776 A1 | 12/2010 | Salahieh et al. |
| 2011/0112630 A1 | 5/2011 | Groothuis et al. |
| 2011/0166566 A1 | 7/2011 | Gabriel |
| 2012/0022640 A1 | 1/2012 | Gross et al. |
| 2012/0290064 A1 | 11/2012 | Fargahi |
| 2012/0316639 A1 | 12/2012 | Kleinschrodt |
| 2012/0330408 A1 | 12/2012 | Hillukka et al. |
| 2014/0107693 A1 | 4/2014 | Plassman |
| 2014/0324164 A1 | 10/2014 | Gross et al. |
| 2015/0088189 A1 | 3/2015 | Paul, Jr. |
| 2015/0112430 A1 | 4/2015 | Creaven et al. |
| 2016/0045311 A1 | 2/2016 | McCann et al. |
| 2018/0092744 A1 | 4/2018 | von Oepen et al. |

FOREIGN PATENT DOCUMENTS

| | | |
|---|---|---|
| EP | 2702965 | 3/2014 |
| JP | 2003062072 | 3/2003 |
| WO | WO 2007044285 | 4/2007 |
| WO | WO 2007136829 | 11/2007 |
| WO | WO 2008103722 | 8/2008 |
| WO | WO 2010121076 | 10/2010 |
| WO | WO 2012020521 | 2/2012 |
| WO | WO 2014121280 | 8/2014 |
| WO | WO 2014128705 | 8/2014 |
| WO | WO 2016112085 | 7/2016 |
| WO | WO 2016144708 | 9/2016 |
| WO | WO 2016150806 | 9/2016 |
| WO | WO 2018093426 | 5/2018 |

OTHER PUBLICATIONS

U.S. Appl. No. 15/662,014, May 31, 2019, OA.
U.S. Appl. No. 15/662,014, Oct. 2, 2019, NOA.
U.S. Appl. No. 15/662,014, Jan. 23, 2019, NOA.

* cited by examiner

DELIVERY CATHETER DISTAL CAP

CROSS-REFERENCE TO RELATED APPLICATIONS

This application is a continuation of U.S. patent application Ser. No. 15/662,014, filed Jul. 27, 2017, entitled "Delivery Catheter Distal Cap", which claims priority to and the benefit of: U.S. Patent Application Ser. No. 62/422,426, filed Nov. 15, 2016, entitled "Delivery Catheter Distal Cap", the disclosures of which are incorporated herein by this reference in their entireties.

BACKGROUND OF THE DISCLOSURE

Intravascular medical procedures allow the performance of therapeutic treatments in a variety of locations within a patient's body while requiring only relatively small access incisions. An intravascular procedure may, for example, eliminate the need for open-heart surgery, reducing risks, costs, and time associated with an open-heart procedure. The intravascular procedure also enables faster recovery times with lower associated costs and risks of complication. An example of an intravascular procedure that significantly reduces procedure and recovery time and cost over conventional open surgery is a heart valve replacement or repair procedure. An artificial valve is guided to the heart through the patient's vasculature. For example, a catheter is inserted into the patient's vasculature and directed to the inferior vena cava. The catheter is then urged through the inferior vena cava toward the heart by applying force longitudinally to the catheter. Upon entering the heart from the inferior vena cava, the catheter enters the right atrium. The distal end of the catheter may be deflected by one or more wires positioned inside the catheter. Precise control of the distal end of the catheter allows for more reliable and faster positioning of a medical device and/or implant and other improvements in the procedures.

The devices can also be directed through the valve chordae or papillary muscles, for example, for interventional therapy to the mitral valve. When such procedures require the use of more than one instrument, each instrument would be dependent upon proper positioning in relation to the valve. Therefore, positioning or steering mechanisms need to be built into each instrument. This adds further cost, complexity, and time to the procedures.

Other procedures may include tracking a catheter and/or access sheath from a puncture in the femoral vein through the intra-atrial septum to the left atrium. This pathway may be used to access the left atrium for ablation of the atrium wall or ablation around the pulmonary veins. Such interventional therapies would require precise alignment with target areas for proper ablation placement. Additionally, alternative access routes and/or access routes to other cavities may be desired.

The scope of intravascular procedures has increased in recent years with more intravascular devices delivered to the heart through the patient's vasculature. Larger and more rigid intravascular devices are used that introduce additional complications to the navigation, delivery, and deployment of the intravascular device. Retention and deployment mechanisms that support a variety of larger or more rigid intravascular devices are desirable.

BRIEF SUMMARY OF THE DISCLOSURE

In an embodiment, an intravascular device delivery system includes an elongated member and a distal end cap. The elongated member includes at least a delivery catheter. The distal end cap is located at a distal end of the delivery catheter. The distal end cap includes at least one channel and at least one connection member located in the channel. The at least one connection member is configured to move radially relative to the distal end cap within the at least one channel between a retracted position and an extend position.

In another embodiment, the intravascular device delivery system includes at least one tension cable operably coupled to the at least one connection member. The tension cable is configured to transmit a tension force through the tension cable and apply a radially inward force to the at least one connection member to move the at least one connection member toward the retracted position.

In yet another embodiment, the intravascular device delivery system includes an intravascular device with at least one recess therein. The at least one recess is configured to receive the at least one connection member.

This summary is provided to introduce a selection of concepts that are further described below in the detailed description. This summary is not intended to identify specific features of the claimed subject matter, nor is it intended to be used as an aid in limiting the scope of the claimed subject matter.

Additional features of embodiments of the disclosure will be set forth in the description which follows. The features of such embodiments may be realized by means of the instruments and combinations particularly pointed out in the appended claims. These and other features will become more fully apparent from the following description and appended claims, or may be learned by the practice of such exemplary embodiments as set forth hereinafter.

BRIEF DESCRIPTION OF THE DRAWINGS

In order to describe the manner in which the above-recited and other features of the disclosure can be obtained, a more particular description will be rendered by reference to specific embodiments thereof which are illustrated in the appended drawings. For better understanding, the like elements have been designated by like reference numbers throughout the various accompanying figures. While some of the drawings may be schematic or exaggerated representations of concepts, at least some of the drawings may be drawn to scale. Understanding that the drawings depict some example embodiments, the embodiments will be described and explained with additional specificity and detail through the use of the accompanying drawings in which.

DETAILED DESCRIPTION

Figure 1:
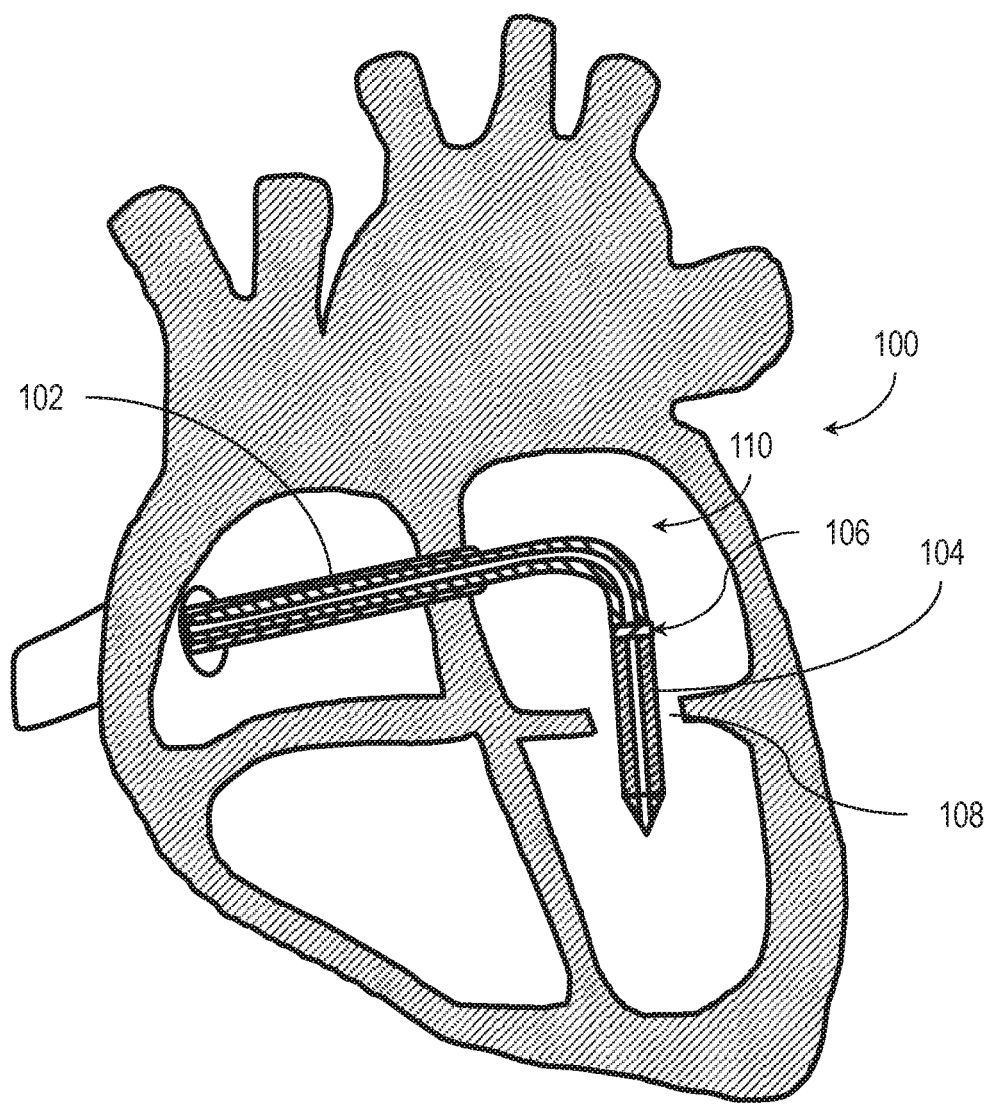
FIG. 1 is a schematic representation of an intravascular device positioned in a heart by an intravascular device delivery system, according to the present disclosure.

One or more specific embodiments of the present disclosure will be described below. In an effort to provide a concise description of these embodiments, some features of an actual embodiment may or may not be described in the specification. It should be appreciated that in the development of any such actual embodiment, as in any engineering or design project, numerous embodiment-specific decisions will be made to achieve the developers' specific goals, such as compliance with system-related and business-related constraints, which may vary from one embodiment to another. It should further be appreciated that such a development effort might be complex and time consuming, but would nevertheless be a routine undertaking of design, fabrication, and manufacture for those of ordinary skill having the benefit of this disclosure.

One or more embodiments of the present disclosure may generally relate to manufacturing and using intravascular device delivery systems or other steerable intravascular system. An intravascular device delivery system may allow a medical professional to deliver an intravascular or other medical device to a target location in a patient's body. While the present disclosure will describe intravascular device delivery systems and applications thereof in relation to intravascular procedures in the heart, it should be understood that the devices, systems, and methods described herein may be applicable to other bodily lumens and/or cavities. Additionally, elements described in relation to any embodiment depicted and/or described herein may be combinable with elements described in relation to any other embodiment depicted and/or described herein. For example, any element described in relation to an embodiment depicted in FIG. 1 may be combinable with any element of an embodiment described in FIG. 3, and any element described in relation to an embodiment described in FIG. 5 may be combinable with any element of an embodiment depicted in FIG. 2.

An intravascular device delivery system includes a flexible elongated member that has a distal end and a proximal end. A handle is connected to a proximal end of the elongated member to allow a user, such as a medical professional and/or clinician, to control one or more movements of the elongated member. An intravascular device is positioned at and/or connected to the distal end of the elongated member.

In some embodiments, the elongated member includes a plurality of elements. For example, the elongated member may include a plurality of elements that extend from the proximal end to the distal end. In some embodiments, at least one of the elements of the elongated member includes a plurality of lumens therethrough to allow steerability of the element. In at least one embodiment, at least one element of the elongated member is steerable in at least two planes.

In some embodiments, the handle may include one or more controls (e.g., a knob, a button, a lever, or other controls) that may move at least one part of the intravascular device delivery system relative to another. For example, the handle may include one or more controls for moving at least one element of the elongated member relative to another element of the elongated member. The handle may move an inner element relative to an outer element of the elongated member in a proximal direction, in a distal direction, in a rotational direction, or combinations thereof.

FIG. 1 illustrates an intravascular device delivery system 100 that includes an elongated member 102 with an intravascular device 104 connected to a distal end of the elongated member 102. In some embodiments, the intravascular device 104 is selectively coupled to the elongated member 102 by a distal end cap 106 on the elongated member 102. The distal end cap 106 may substantially retain the intravascular device 104 relative to the distal end of the elongated member 102 until the intravascular device 104 is positioned adjacent a target location 108. In some embodiments, the target location 108 may be in a heart 110, such as a mitral annulus of the heart 110. For example, the intravascular device 104 may be a valve repair or valve replacement device configured to repair and/or replace a mitral valve of the heart 110.

In some embodiments, the intravascular device 104 has a diameter larger than an inner diameter of the elongated member 102. In such embodiments, the intravascular device 104 may not be deliverable through the elongated member 102 from outside of the patient's body. The intravascular device 104 may, instead, be guided to the target location 108 externally to at least a portion of the elongated member 102. For example, the intravascular device 104 may be delivered to the target location 108 by positioning the intravascular device 104 on or at a distal end of the elongated member 102 and navigating the intravascular device 104 and elongated member 102 through the patient's vasculature.

Upon positioning the intravascular device 104 at the target location 108, the intravascular device 104 may be decoupled from the elongated member 102. In some embodiments, the distal end cap 106 may have one or more connection members that may selectively engage with the intravascular device 104. Upon disengaging the one or more connection members, the distal end cap 106 may deploy the intravascular device 104 at the target location 108.

Figure 2:
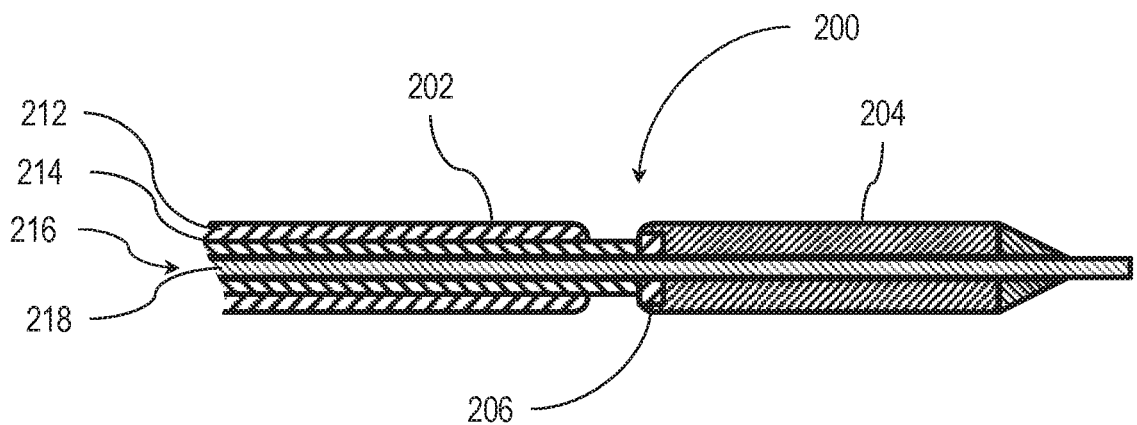
FIG. 2 is a side cross-sectional view of an embodiment of a distal end cap in an intravascular device delivery system, according to the present disclosure.

As shown in FIG. 2, in some embodiments an elongated member 202 includes at least a steerable catheter 212 and a delivery catheter 214 with a lumen 216 extending therethrough in a longitudinal direction. In some embodiments, the lumen 216 is configured to receive a guidewire 218 therein that extends through the longitudinal length of the elongated member 202 and through a distal end cap 206. In at least one embodiment, the guidewire 218 extends through an intravascular device 204.

In some embodiments, the steerable catheter 212 may have one or more steering cables therein that allow the steerable catheter 212 to be deflected in at least one plane to direct the elongated member 202 and/or intravascular device 204 through the patient's vasculature. In other embodiments, the elongated member may include a plurality of steerable catheters that are each deflectable in at least one plane.

The elongated member 202 also includes a delivery catheter 214 coupled to a distal end cap 206. In some embodiments, the delivery catheter 214 may be a steerable catheter that is deflectable in at least one plane. In other embodiments, the delivery catheter 214 may not have any steering cables or other elements that may deflect the delivery catheter 214. In such embodiments, the direction of the delivery catheter 214 may be influenced by the steerable catheter 212 and the delivery catheter 214 may be movable longitudinally relative to the steerable catheter 212.

As shown in FIG. 2, at least part of the distal end cap 206 may be located radially within a portion of the intravascular device 204. In some embodiments, the distal end cap 206 is located radially within a portion of a body of the intravascular device 204. In other embodiments, the distal end cap 206 is located radially within an outer sleeve of the intravascular device 204. For example, the intravascular device 204 may be a self-expanding device (i.e., a Nitinol or other shape-memory device) that is held in a compressed state during delivery by an outer sleeve. Upon removal of the outer sleeve, the self-expanding device may expand to an expanded state. In some embodiments, the distal end cap 206 may engage with the intravascular device 204 and limit and/or prevent movement of the intravascular device 204 relative to the distal end cap 206. In other embodiments, the distal end cap 206 may engage with an outer sleeve positioned radially outside the intravascular device 204 and limit and/or prevent movement of the outer sleeve relative to the distal end cap 206.

Figure 3:
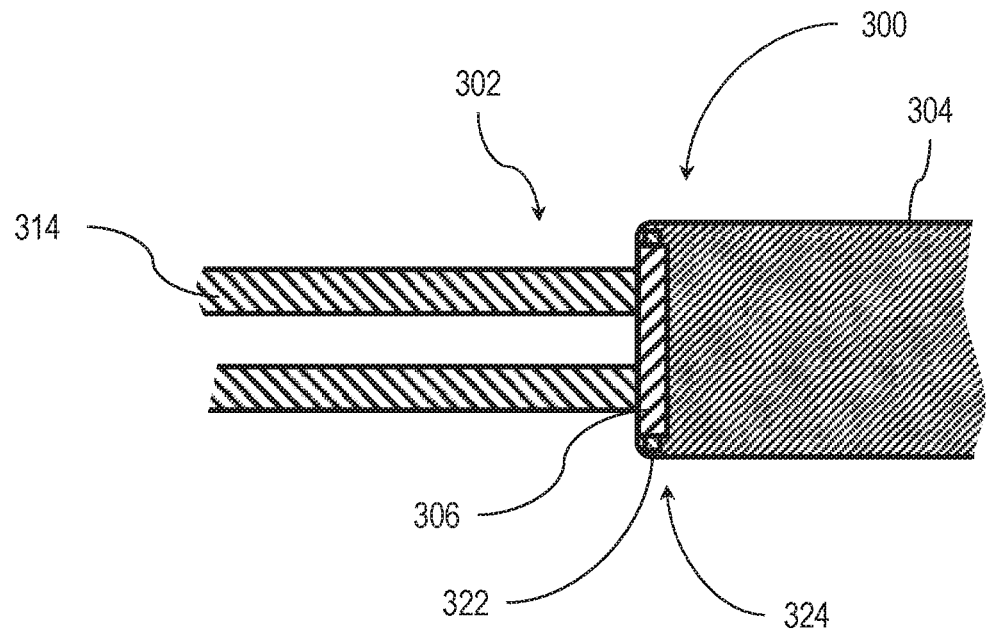
FIG. 3 is a detail cross-sectional view of another embodiment of a distal end cap retaining an intravascular device, according to the present disclosure.

FIG. 3 illustrates an embodiment of a connection mechanism in an intravascular device delivery system 300 between a distal end cap 306 and an intravascular device 304. The distal end cap 306 may be positioned at and fixed relative to a distal end of a delivery catheter 314 of an elongated member 302. The distal end cap 306 may selectively engage with the intravascular device 304 via a mechanical interlock.

In some embodiments, the distal end cap 306 has one or more connection members 322 that protrude at least partially radially and outward from the distal end cap 306. The one or more connection members 322 may be received by one or more recesses 324 in the intravascular device 304. In other embodiments, the one or more connection members 322 may be received by one or more recesses 324 in an outer sleeve around the intravascular device 304. In some embodiments, the arrangement of the one or more connection members 322 and the one or more recesses 324 are reversed such that the one or more connection members 322 are associated with the intravascular device 304 (e.g., a body or sleeve thereof) and the one or more recesses 324 are formed in the distal end cap 306.

In some embodiments, the one or more connection members 322 are a plurality of connection members movable relative to the distal end cap 306. In other embodiments, the one or more connection members 322 are a single annular connection member movable relative to the distal end cap 306, such as a compressible ring.

In some embodiments, the one or more recesses 324 are a plurality of recesses. In other embodiments, the one or more recesses 324 are a single annular recess in the intravascular device 304 or outer sleeve associated therewith.

Figure 4:
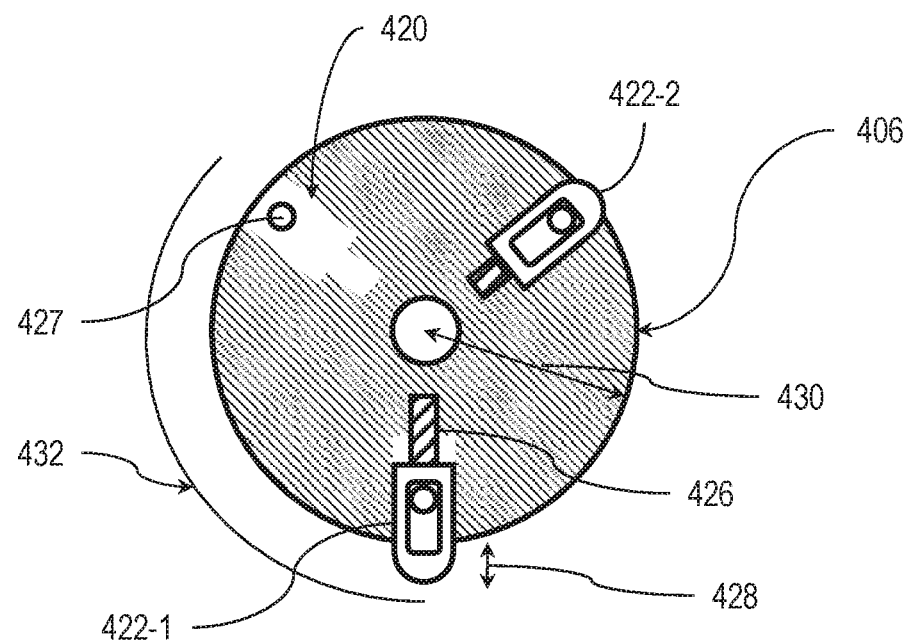
FIG. 4 is an end cross-sectional view of the embodiment of the distal end cap of FIG. 3, according to the present disclosure.

FIG. 4 is an end view (i.e., viewed from the distal end looking toward the proximal direction) illustrating yet another embodiment of a distal end cap 406, according to the present disclosure. The distal end cap 406 may have a plurality of connection members 422 (e.g., connection members 422-1, 422-2) positioned at least partially within the distal end cap 406 and movable in a radial direction relative to the distal end cap 406.

In some embodiments, at least one connection member 422 is movable in a radial direction within a channel 420 or other recess in the distal end cap 406. The at least one connection member 422 may be retained within the channel 420, and therefore within the distal end cap, by a retention member 427 located in the channel 420. For example, the channel 420 may have a cross pin that is received in the connection member 422, limiting the movement of the connection member 422 in the radial direction relative to the distal end cap 406.

At least one of the connection members 422 may be movable between an extended position and a retracted position. As shown in FIG. 4, a first connection member 422-1 is illustrated in an extended position. The first connection member 422-1 may be biased toward the extended position by a biasing element 426. In some embodiments, the biasing element 426 is a compressible fluid, a gel, a polymer bushing, a coil spring, a leaf spring, other resilient element, or combinations thereof. For example, the biasing element 426 may be a rubber block that is compressible and provides a biasing force to urge the first connection member 422-1 toward the extended position.

A second connection member 422-2 shown in FIG. 4 illustrates a retracted position of the second connection member 422-2. While the second connection member 422-2 is shown with at least a portion of the second connection member 422-2 protruding from the distal end cap 406 in the radial direction in the retracted position, it should be understood that, in other embodiments, while in a retracted position, the radially outermost portion of a connection member 422 may be radially within the distal end cap 406. In other embodiments, the radially outermost portion of a connection member 422 may be flush with a radially outer surface of the distal end cap 406.

The radial distance between the retracted position and the extended position may define a radial displacement length 428. In some embodiments, at least one connection member 422 has a radial displacement length 428 that is a percentage of the distal end cap radius 430 in a range having an upper value, a lower value, or upper and lower values 5%, 10%, 15%, 20%, 25%, 30%, 35%, 40%, 45%, 50%, 55%, 60%, 65%, 70%, or any values therebetween. For example, at least one connection member 422 has a radial displacement length 428 that is greater than 5% of the distal end cap radius 430. In other examples, at least one connection member 422 has a radial displacement length 428 that is less than 70% of the distal end cap radius 430. In yet other examples, at least one connection member 422 has a radial displacement length 428 that is between 10% and 65% of the distal end cap radius 430. In further examples, at least one connection member 422 has a radial displacement length 428 that is between 15% and 50% of the distal end cap radius 430. In at least one example, at least one connection member 422 has a radial displacement length 428 about 30% of the distal end cap radius 430.

In some embodiments, the connection members 422 and/or channels 420 are positioned circumferentially about the distal end cap 406 at equal angular intervals. In other embodiments, the connection members 422 and/or channels 420 are positioned circumferentially about the distal end cap 406 at unequal angular intervals. In yet other embodiments, at least two of the connection members 422 and/or channels 420 are spaced at an angular interval 432 in a range having an upper value, a lower value, or upper and lower values including any of 5°, 10°, 15°, 20°, 25°, 30°, 35°, 40°, 45°, 50°, 55°, 60°, 65°, 70°, 75°, 80°, 85°, 90°, 95°, 100°, 105°, 110°, 115°, 120°, 125°, 130°, 135°, 140°, 145°, 150°, 155°, 160°, 165°, 170°, 175°, 180°, or any values therebetween.

For example, at least two of the connection members 422 and/or channels 420 can be spaced at an angular interval 432 greater than 5°. In other examples, at least two of the connection members 422 and/or channels 420 are spaced at an angular interval 432 less than 180°. In yet other examples, at least two of the connection members 422 and/or channels 420 are spaced at an angular interval 432 between 5° and 180°. In further examples, at least two of the connection members 422 and/or channels 420 are spaced at an angular interval 432 between 30° and 150°. In at least one embodiment, at least two of the connection members 422 and/or channels 420 are spaced at an angular interval 432 between 90° and 120°.

Figure 5:
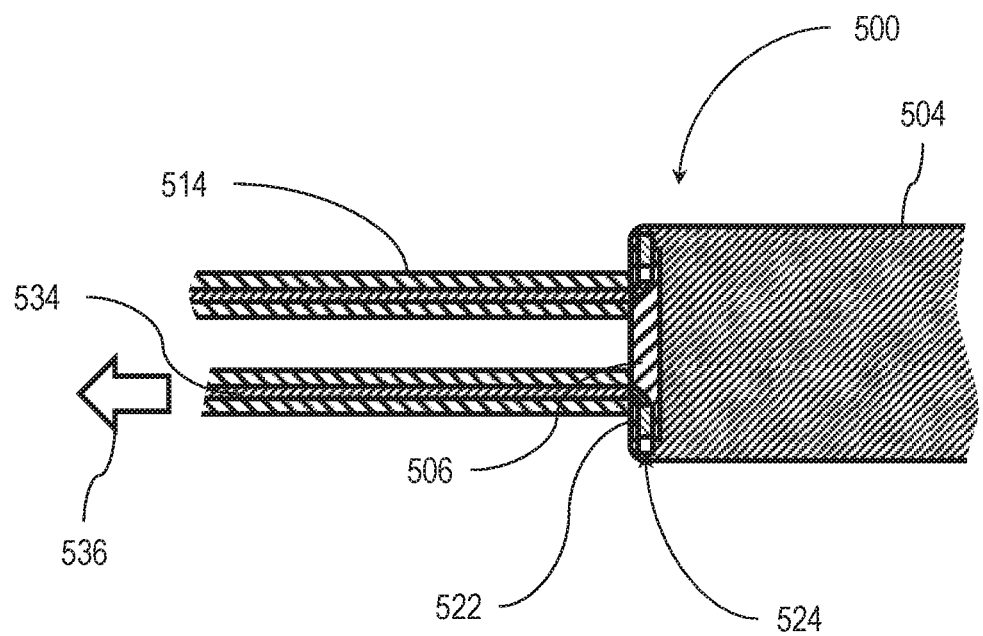
FIG. 5 is a side cross-sectional view of yet another embodiment of a distal end cap, according to the present disclosure.

FIG. 5 is a side cross-sectional view of a further embodiment of an intravascular device delivery system 500 with a distal end cap 506, according to the present disclosure. In some embodiments, a delivery catheter 514 of an intravascular device delivery system 500 includes one or more tension cables 534. The tension cable 534 may extend through a lumen in the wall of the delivery catheter 514 and to the distal end cap 506. In some embodiments, the tension cable 534 is operably connected to and/or in communication with at least one of the connection members 522. A proximal tension force 536 applied to the tension cable 534 may be transmitted through the tension cable 534 to apply a radially inward force to the connection member 522 and move the connection member 522 radially inward toward the distal end cap 506 and away from and/or out of the recess 524 in the intravascular device 504 in the retracted position.

In some embodiments, the proximal tension force 536 is reduced and/or removed from the tension cable 534 and at least one of the connection members 522 may return to an extended position. For example, a biasing element, such as biasing element 426 described in relation to FIG. 4, may urge the connection member 522 toward the extended position and into the recess 524. In at least one embodiment, the connection member 522 moving from the retracted position toward the extended position allows for reconnection of the intravascular device 504 during delivery and/or deployment for repositioning of the intravascular device 504.

In some embodiments, at least one tension cable 534 may be a wire or plurality of wires including or made of tungsten, steel, titanium alloy, aluminum alloy, nickel alloy, other metals, a shape memory material (such as a shape memory alloy or shape memory polymer), inorganic polymer, organic polymer, glasses, ceramics, carbon materials, or other flexible material with sufficient tensile strength. For example, at least one tension cable 534 may be a braided steel cable. In another example, at least one tension cable 534 may be an extruded polymer strand or made of multiple extruded polymer strands interwoven to form an elongate structure, such as a suture or rope. Instead of extruding the strands, the strands can be spun out of solution. In yet another example, at least one tension cable 534 may be a polymer core with metal wires braided around the core.

In some embodiments, at least one tension cable 534 may have a tensile strength in a range having an upper value, a lower value, or an upper and lower value including any of 2 pounds, 4 pounds, 6 pounds, 8 pounds, 10 pounds, 12 pounds, 15 pounds, 20 pounds, 25 pounds, 30 pounds, 40 pounds, 50 pounds, 60 pounds, 70 pounds, 80 pounds, 90 pounds, 100 pounds, or any values therebetween. For example, at least one tension cable 534 may have a tensile strength greater than 2 pounds. In other examples, at least one tension cable 534 may have a tensile strength less than 100 pounds. In yet other examples, at least one tension cable 534 may have a tensile strength in a range of 12 pounds to 100 pounds. In further examples, at least one tension cable 534 may have a tensile strength in a range of 20 pounds to 80 pounds. In at least one example, at least one tension cable 534 may have a tensile strength greater than 40 pounds.

In at least one embodiment, a distal end cap according to the present disclosure may provide a selective connection point between an elongated member and an intravascular device. In at least another embodiment, a distal end cap according to the present disclosure may be selectively decouplable from the intravascular device and transmit torque to the intravascular device. In at least yet another embodiment, a distal end cap according to the present disclosure may allow for reconnection to an intravascular device during or after deployment of the intravascular device.

The articles "a," "an," and "the" are intended to mean that there are one or more of the elements in the associated descriptions. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. Numbers, percentages, ratios, or other values stated herein are intended to include that value, and also other values that are "about" or "approximately" the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing or production process, and may include values that are within 5%, within 1%, within 0.1%, or within 0.01% of a stated value.

A person having ordinary skill in the art should realize in view of the present disclosure that equivalent constructions do not depart from the spirit and scope of the present disclosure, and that various changes, substitutions, and alterations may be made to embodiments disclosed herein without departing from the spirit and scope of the present disclosure. Equivalent constructions, including functional "means-plus-function" clauses are intended to cover the structures described herein as performing the recited function, including both structural equivalents that operate in the same manner, and equivalent structures that provide the same function. It is the express intention of the applicant not to invoke means-plus-function or other functional claiming for any claim except for those in which the words 'means for' appear together with an associated function. Each addition, deletion, and modification to the embodiments that falls within the meaning and scope of the claims is to be embraced by the claims.

The terms "approximately," "about," and "substantially" as used herein represent an amount close to the stated amount that still performs a desired function or achieves a desired result. For example, the terms "approximately," "about," and "substantially" may refer to an amount that is within less than 5% of, within less than 1% of, within less than 0.1% of, and within less than 0.01% of a stated amount. Further, it should be understood that any directions or reference frames in the preceding description are merely relative directions or movements. For example, any references to "up" and "down" or "above" or "below" are merely descriptive of the relative position or movement of the related elements.

The present disclosure may be embodied in other specific forms without departing from its spirit or characteristics. The described embodiments are to be considered as illustrative and not restrictive. The scope of the disclosure is, therefore, indicated by the appended claims rather than by the foregoing description. Changes that come within the meaning and range of equivalency of the claims are to be embraced within their scope.

What is claimed is:

1. A method of delivering an intravascular device to a target location, the method comprising:
   navigating an intravascular device delivery system to the target location, the intravascular device delivery system comprising:
      an elongated member, the elongated member including a delivery catheter and a longitudinal axis; and
      a distal end cap located at a distal end of the delivery catheter, the distal end cap including:
         a radially elongate channel, the radially elongate channel extending generally transversely to the longitudinal axis, and a connection member located in the radially elongate channel, the connection member configured to move radially within the radially elongate channel between a retracted position and an extended position; and decoupling the intravascular device from the intravascular device delivery system.

2. The method of claim 1, wherein the target location is within a heart.

3. The method of claim 1, wherein the connection is biased within the radially elongate channel.

4. The method of claim 1, wherein decoupling the intravascular device comprises overcoming a biasing force applied to the connection member to move the connection member within the radially elongate channel.

5. The method of claim 1, wherein decoupling the intravascular device comprises applying a radial inward force to the connection member.

6. The method of claim 5, wherein applying the radial inward force comprises retracting a tension cable.

7. The method of claim 1, wherein navigating the intravascular device delivery system comprises steering a steering catheter of the intravascular device.

8. The method of claim 7, wherein steering the steering catheter comprises deflecting the steering catheter in at least one plane.

9. A method of delivering an intravascular device to a target location, the method comprising:

navigating an intravascular device delivery system to a target location within a heart, the intravascular device delivery system comprising:

an elongated member, the elongated member including a delivery catheter and a longitudinal axis; and a distal end cap located at a distal end of the delivery catheter, the distal end cap including:

a plurality of radially elongate channels, each of the plurality of radially elongate channels extending generally transversely to the longitudinal axis, and a plurality of connection members each being located in one of the plurality of radially elongate channels, each connection member being configured to move radially within a respective radially elongate channel between a retracted position and an extended position, each connection member being biased in the extended position; and decoupling the intravascular device from the intravascular device delivery system by moving the plurality of connection members from the extended position to the retracted position.

10. The method of claim 9, wherein the plurality of connection members are spaced circumferentially about the distal end cap at equal angular intervals.

11. The method of claim 9, wherein at least two of the plurality of connection members are spaced at an angular interval between 5° and 180°.

12. The method of claim 9, further comprising a biasing element disposed within each radially elongate channel.

13. The method of claim 12, wherein the biasing element is a spring.

14. The method of claim 9, further comprising a resilient member associated within each radially elongate channel and being configured to limit radial movement of the connection member within the radially elongate channel.

15. The method of claim 9, wherein each connection member has a radial displacement length defined as a distance between a radially outermost portion of the connection member in the extended position and the radially outermost portion of the connection member in the retracted position, the radial displacement length being between about 5% and 70% of a distal end cap radius.

16. A method of delivering an intravascular device to a target location, the method comprising:

navigating an intravascular device delivery system through a patient's vasculature to a target location within a heart, the intravascular device delivery system comprising:

an elongated member, the elongated member including a delivery catheter and a longitudinal axis;

a distal end cap located at a distal end of the delivery catheter, the distal end cap including:

a plurality of radially elongate channels, each of the plurality of radially elongate channels extending generally transversely to the longitudinal axis, and a plurality of connection members each being located in one of the plurality of radially elongate channels, each connection member being configured to move radially within a respective radially elongate channel between a retracted position and an extended position, each connection member being biased in the extended position; and an intravascular device positioned at least partially radially around the distal end cap and longitudinally overlapping the distal end cap;

decoupling the intravascular device from the intravascular device delivery system by moving the plurality of connection members from the extended position to the retracted position.

17. The method of claim 16, wherein a radially outermost portion of a connection member of the plurality of connection members is radially within the distal end cap in the retracted position.

18. The method of claim 17, wherein the intravascular device is a valve replacement device or a valve repair device.

19. The method of claim 18, wherein decoupling the intravascular device comprises applying a radial inward force to each of the plurality of connection members.

20. The method of claim 19, wherein applying the radial inward force comprises proximally moving a plurality of tension cables that are disposed within a lumen wall of a delivery catheter of the intravascular device delivery system.

* * * * *